(12) United States Patent
Zhang et al.

(10) Patent No.: US 12,742,713 B2
(45) Date of Patent: Sep. 22, 2026

(54) METHOD FOR EVALUATING ROCK COMPRESSIVE STRENGTH BASED ON CUTTINGS MINERAL COMPOSITION, NANO-INDENTATION, AND FRICTION TESTS

(71) Applicant: Southwest Petroleum University, Chengdu (CN)

(72) Inventors: Qiangui Zhang, Jintang (CN); Xiangyu Fan, Chengdu (CN); Cheng Meng, Ziyang (CN); Hongxi Li, Chengdu (CN); Tianshou Ma, Chengdu (CN); Zhilin Li, Deyang (CN); Pengfei Zhao, Chengdu (CN); Zhuzheng Li, Pengzhou (CN); Lichun Jia, Pengzhou (CN); Yufei Chen, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 19/649,095

(22) Filed: Apr. 15, 2026

(65) Prior Publication Data

US 2026/0243642 A1 Aug. 20, 2026

(30) Foreign Application Priority Data

Jul. 26, 2025 (CN) ........................ 202511036253.9

(51) Int. Cl.
*G01N 3/42* (2006.01)
*G01N 19/02* (2006.01)
*G01N 33/24* (2006.01)

(52) U.S. Cl.
CPC ............... *G01N 3/42* (2013.01); *G01N 19/02* (2013.01); *G01N 33/24* (2013.01);
(Continued)

(58) Field of Classification Search
CPC .......... G01N 3/42; G01N 19/02; G01N 33/24; G01N 2203/0067; G01N 2203/0075; G01N 2203/0078
See application file for complete search history.

(56) References Cited

U.S. PATENT DOCUMENTS

2021/0116341 A1 4/2021 Zhang

FOREIGN PATENT DOCUMENTS

| | | | | |
|---|---|---|---|---|
| CN | 110186755 A | * | 8/2019 | ............... G01N 9/02 |
| CN | 112179770 A | * | 1/2021 | ............... G01N 1/44 |
| CN | 116908024 A | * | 10/2023 | ............... G01N 3/40 |
| CN | 117672387 A | * | 3/2024 | ............ G06T 17/20 |

(Continued)

OTHER PUBLICATIONS

"Upscaling of Mechanical Properties of Shale Rocks from Microscale to Mesoscale by 2D Finite Element Method", Kong, L. et al., Journal of the Society of Petroleum Engineers, May 2026 (pp. 3200-3215). (Year: 2026).*

"Upscaling Characterization of Mechanical Properties of Shale Based on the Constrained Big Data Nanoindentation", Zhang, M. et al., Journal of the Society of Petroleum Engineers, May 2026 (pp. 3105-3122). (Year: 2026).*

(Continued)

*Primary Examiner* — Natalie Huls
(74) *Attorney, Agent, or Firm* — Birchwood IP

(57) ABSTRACT

The present application discloses a method for evaluating rock compressive strength based on cuttings mineral composition, nano-indentation, and friction tests, relating to the field of petroleum and natural gas exploration and development. Specifically, relative contents of rock minerals, average nano-indentation crack lengths, nano-indentation load-displacement curves of each rock mineral, and rock friction coefficient are first obtained through rock X-ray diffraction experiments, nano-indentation experiments, and friction tests; subsequently, based on the principle of energy conservation, elastic modulus of each rock mineral and plane-
(Continued)

strain fracture toughness of each rock mineral are calculated; then, according to the principle of weighted superposition, each mineral parameter is weighted and integrated based on a proportion to obtain rock failure characteristic parameters; finally, uniaxial and triaxial compressive strength of the rock are calculated in combination with the rock failure characteristic parameters and the rock friction coefficient.

5 Claims, 6 Drawing Sheets

(52) U.S. Cl.
CPC ................ *G01N 2203/0067* (2013.01); *G01N 2203/0075* (2013.01); *G01N 2203/0078* (2013.01)

(56) References Cited

FOREIGN PATENT DOCUMENTS

| | | | | | |
|---|---|---|---|---|---|
| CN | 118958961 | A | | 11/2024 | |
| CN | 119198230 | A | | 12/2024 | |
| CN | 119688456 | A | * | 3/2025 | |
| CN | 120020523 | A | * | 5/2025 | ............ G06F 18/15 |
| KR | 20150007884 | A | | 1/2015 | |

OTHER PUBLICATIONS

"Geomechanics field characterization of Woodford Shale and Barnett Shale with advanced logging tools and nano-indentation on drill cuttings", Abousleiman, Y. et al., The Leading Edge, Jun. 2010 (pp. 730-736). (Year: 2010).*

* cited by examiner

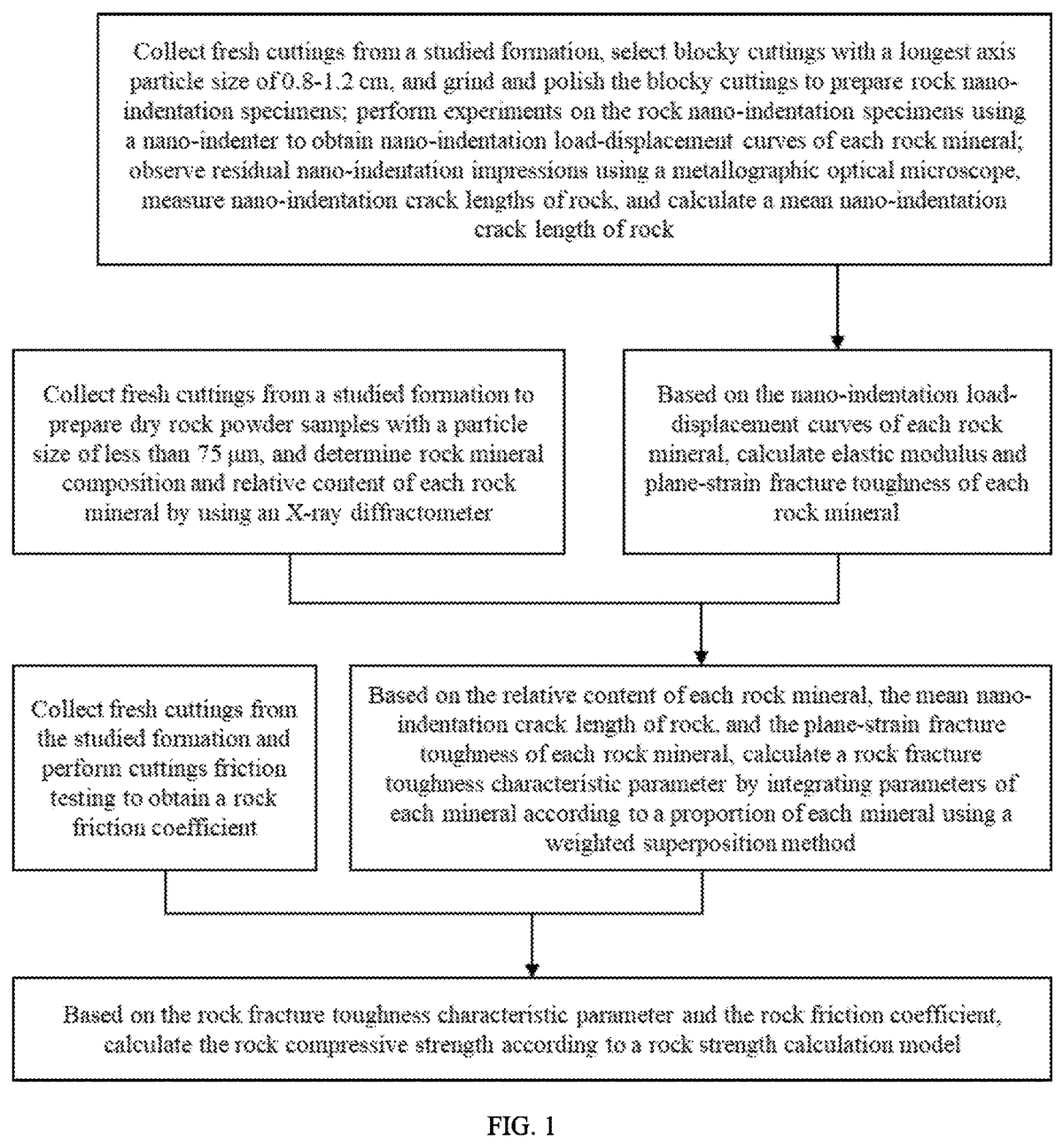

Collect fresh cuttings from a studied formation, select blocky cuttings with a longest axis particle size of 0.8-1.2 cm, and grind and polish the blocky cuttings to prepare rock nano-indentation specimens; perform experiments on the rock nano-indentation specimens using a nano-indenter to obtain nano-indentation load-displacement curves of each rock mineral; observe residual nano-indentation impressions using a metallographic optical microscope, measure nano-indentation crack lengths of rock, and calculate a mean nano-indentation crack length of rock Collect fresh cuttings from a studied formation to prepare dry rock powder samples with a particle size of less than 75 μm, and determine rock mineral composition and relative content of each rock mineral by using an X-ray diffractometer Based on the nano-indentation load-displacement curves of each rock mineral, calculate elastic modulus and plane-strain fracture toughness of each rock mineral Collect fresh cuttings from the studied formation and perform cuttings friction testing to obtain a rock friction coefficient Based on the relative content of each rock mineral, the mean nano-indentation crack length of rock, and the plane-strain fracture toughness of each rock mineral, calculate a rock fracture toughness characteristic parameter by integrating parameters of each mineral according to a proportion of each mineral using a weighted superposition method Based on the rock fracture toughness characteristic parameter and the rock friction coefficient, calculate the rock compressive strength according to a rock strength calculation model

FIG. 1

| Rock type | Clay minerals (%) | Quartz (%) | Feldspar (%) | Calcite (%) | Dolomite (%) |
|---|---|---|---|---|---|
| Shale | 15.9 | 20.7 | 25.5 | 23.7 | 14.2 |
| Dolostone | 0.5 | 0.1 | 0.4 | 0.7 | 98.3 |
FIG. 2
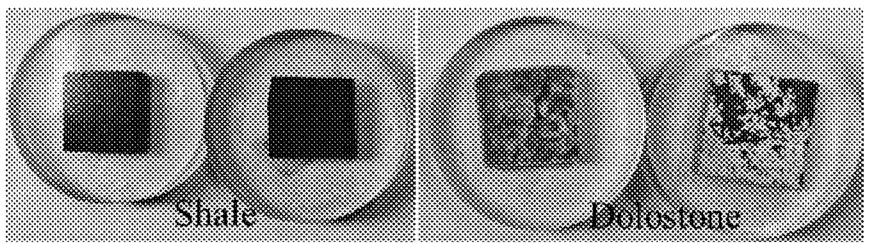
FIG. 3
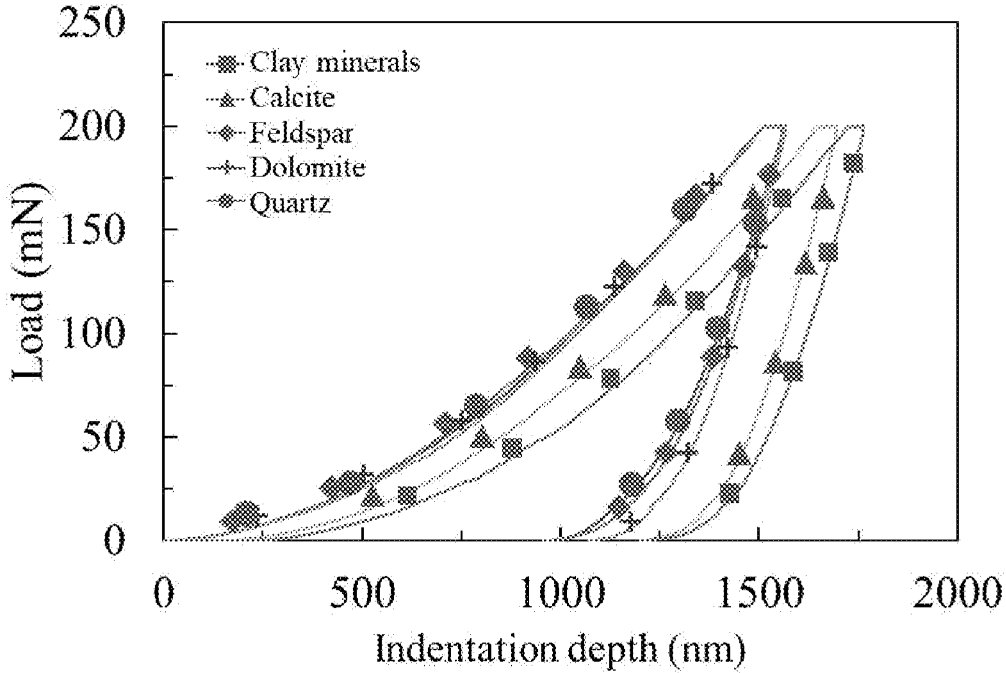
FIG. 4

| Parameter | Shale | | | | | Dolostone |
|---|---|---|---|---|---|---|
| | Clay minerals | Quartz | Dolomite | Calcite | Feldspar | Dolomite |
| Fitting equation of load-displacement curve during loading stage, $P_l$ | $P_{l1}=200\times\left(\frac{h_1}{2620}\right)^{1.52}$ | $P_{l2}=200\times\left(\frac{h_2}{1920}\right)^{1.73}$ | $P_{l3}=200\times\left(\frac{h_3}{1252}\right)^{1.92}$ | $P_{l4}=200\times\left(\frac{h_4}{2127}\right)^{1.69}$ | $P_{l5}=200\times\left(\frac{h_5}{1865}\right)^{1.72}$ | $P_{l6}=200\times\left(\frac{h_6}{1239}\right)^{1.96}$ |
| Fitting equation of load-displacement curve during unloading stage, $P_u$ | $P_{u1}=200\times\left(\frac{h_1-1356}{2652-1356}\right)^{2.25}$ | $P_{u2}=200\times\left(\frac{h_2-1025}{1833-1020}\right)^{1.43}$ | $P_{u3}=200\times\left(\frac{h_3-688}{1386-688}\right)^{1.92}$ | $P_{u4}=200\times\left(\frac{h_4-1138}{2301-1138}\right)^{2.05}$ | $P_{u5}=200\times\left(\frac{h_5-1132}{2012-1132}\right)^{1.56}$ | $P_{u6}=200\times\left(\frac{h_6-708}{1279-708}\right)^{1.96}$ |
| Mean nano-indentation crack length $c$/μm | 12.35 | | | | | 13.01 |
| Total number of indentation cracks $k$ | 22 | | | | | 7 |
| Contact stiffness $S$/mN·nm$^{-1}$ | 300.5 | 424.2 | 475.2 | 351.1 | 397.2 | 467.5 |
| Contact area $A_c$/μm$^2$ | 89.5 | 22.1 | 10.9 | 42.4 | 38.2 | 10.4 |
| Elastic modulus $E$/$GPa$ | 42.85 | 90.28 | 110.04 | 70.61 | 77.16 | 117.42 |
| Total energy $U_t$/mN·μm | 185.6 | 98.4 | 77.2 | 165.8 | 114.8 | 72.9 |
| Elastic energy $U_e$/mN·μm | 100.5 | 52.5 | 43.2 | 97.2 | 62.5 | 44.7 |
| Purely plastic energy $U_{pp}$/mN μm | 83.88 | 45.665 | 33.843 | 67.499 | 51.343 | 28.021 |
| Fracture energy $U_c$/mN·μm | 1.22 | 0.235 | 0.157 | 1.101 | 0.957 | 0.179 |
| Fracture toughness $K_{IC}$/MPa·m$^{0.5}$ | 0.314 | 0.739 | 0.781 | 0.667 | 0.653 | 0.703 |
| Friction force $F_f$/N | 61.2 | | | | | 70.2 |
| Normal force $F_N$/N | 100 | | | | | 100 |
| Rock friction coefficient $\mu$ | 0.612 | | | | | 0.702 |

FIG. 6

METHOD FOR EVALUATING ROCK COMPRESSIVE STRENGTH BASED ON CUTTINGS MINERAL COMPOSITION, NANO-INDENTATION, AND FRICTION TESTS

CROSS-REFERENCE TO RELATED APPLICATIONS

This application claims priority to Chinese Patent Application No. CN202511036253.9, filed on Jul. 26, 2025, which is hereby incorporated by reference in its entirety.

TECHNICAL FIELD

The present application belongs to the field of petroleum and natural gas exploration and development, and specifically relates to a method for evaluating rock compressive strength based on cuttings mineral composition, nano-indentation, and friction tests.

BACKGROUND

The accurate evaluation of rock mechanical properties is crucial for rock mass engineering construction, particularly because rock compressive strength is a key parameter for conducting rock mass engineering design and directly affects the safety of rock mass engineering structures. Conventional methods for obtaining rock compressive strength involve drilling cores and preparing standard cylindrical rock specimens, followed by conducting uniaxial or triaxial compression tests to obtain measurement results. In addition, some researchers have proposed a plurality of empirical models for evaluating rock compressive strength through a Schmidt hammer test and a point load test. Moreover, artificial intelligence techniques based on physical properties of rock have been attempted to address the evaluation of rock compressive strength, where a relationship between rock mechanical properties and rock acoustic-electrical physical property parameters is first established, and the rock compressive strength is predicted using neural networks and machine learning models. Although the aforementioned methods can obtain relatively accurate rock compressive strength for the studied formations, these methods are generally time-consuming and costly. Such limitations are particularly evident in jointed rock masses or shale formations, because the success rate of preparing standard specimens is low, which increases overall cost and results in substantial waste of valuable rock samples. Therefore, there is an urgent need for a new method capable of reducing dependence on the size and shape of a rock sample, decreasing requirements for large amounts of data and analysis time, and still accurately evaluating rock compressive strength.

With the continuous development of rock surface testing technologies, nano-indentation has been widely applied to study the mechanical behavior of rock at the microscale. This technology imposes low requirements on sample size and does not strictly limit sample shape. This technology applies micro- to milli-Newton loads on the rock specimen surface using a diamond indenter to obtain load-displacement curves from nano-indentation, and determines micro-mechanical parameters of rock, such as elastic modulus, hardness, and fracture toughness, based on characteristics of the load-displacement curves. Extensive research has demonstrated that these micro-mechanical properties, for example, the elastic modulus and hardness of constituent minerals, are strongly correlated with macroscopic rock compressive strength. Accordingly, microscopic mechanical properties measured by nano-indentation can be extended to predict overall rock behavior, such as evaluating rock compressive strength.

To overcome limitations of sample size and shape and to reduce the economic and time costs of evaluating rock compressive strength, and to achieve precise evaluation of rock compressive strength, the present application proposes a method for evaluating rock compressive strength based on cuttings mineral composition, nano-indentation, and friction tests. The method is based on micro-fracture mechanics theory, where a novel approach for evaluating rock compressive strength is constructed by introducing the mean indentation crack length obtained from cuttings nano-indentation experiments and fracture toughness characteristic parameters of rock and combining with the rock friction coefficient obtained from friction tests, thereby enabling precise calculation of rock compressive strength. The theoretical basis of the method for evaluating rock compressive strength based on cuttings mineral composition, nano-indentation, and friction tests is as follows:

1. Critical Condition for Rock Failure

The distribution of microcracks within rock is random. If the tips of all micro-cracks originate from a common point and the directions of the micro-cracks lie within a defined angular range, with increasing external load applied to the rock, the shear force acting on internal crack surfaces may gradually exceed frictional resistance, thereby causing relative sliding along the crack surfaces. Such sliding generates tensile stress concentration at crack tips, potentially inducing crack initiation. Accordingly, a critical condition for rock failure can be established, and a calculation formula is as follows:

$$\frac{1}{2}[(\sigma_1+\sigma_3)-(\sigma_1-\sigma_3)\cos 2\beta-\mu(\sigma_1-\sigma_3)\sin 2\beta]\sqrt{\pi c}\geq K_{IC} \tag{1}$$

where $\sigma_i$ represents maximum principal stress, in MPa; $\sigma_3$ represents minimum principal stress, in MPa; β represents an included angle between the principal stress direction and a crack surface, in °; μ represents a rock friction coefficient, dimensionless; π represents pi, dimensionless; c represents a mean nano-indentation crack length of rock, in μm; and $K_{IC}$ represents rock plane-strain fracture toughness, in $MPa\cdot m^{0.5}$.

The formula (1) can be simplified to:

$$\begin{cases} M_1\tan^2\beta+M_2\tan\beta+M_3\leq 0 \\ M_1=\mu\sigma_1+\dfrac{K_{IC}}{\sqrt{\pi c}} \\ M_2=-(\sigma_1-\sigma_3) \\ M_3=\mu\sigma_3+\dfrac{K_{IC}}{\sqrt{\pi c}} \end{cases} \tag{2}$$

The formula (2) can be solved to obtain:

$$\begin{cases} \tan\beta_1=\dfrac{-M_2-\sqrt{M_2^2-4M_1M_3}}{2M_1} \\ \tan\beta_2=\dfrac{-M_2+\sqrt{M_2^2-4M_1M_3}}{2M_1} \end{cases} \tag{3}$$

Based on a direction of microcrack formation $\varphi=\beta_2-\beta_1$, the following can be obtained:

$$\tan\varphi = \frac{\tan\beta_2 - \tan\beta_1}{1 + \tan\beta_1 \tan\beta_2} = \frac{\sqrt{M_2^2 - 4M_1M_3}}{M_1 + M_2} \tag{4}$$

2. Rock Strength Calculation Model Based on Micro-Fracture Mechanics

To evaluate rock fracture failure, a rock failure characteristic parameter needs to be determined as a criterion for complete rock failure, where the failure characteristic parameter should be an invariant. The rock failure characteristic parameter is defined as $|\partial\cos\varphi/\partial\sigma_1|$.

The formula (4) can first be transformed into:

$$\cos\varphi = \frac{\mu}{\sqrt{1+\mu^2}}\left(1 + \frac{2\sigma_3 + \frac{2K_{IC}}{\mu\sqrt{\pi c}}}{\sigma_1 - \sigma_3}\right) \tag{5}$$

Taking the partial derivative of the formula (5) with respect to $\sigma_1$ yields the rock failure characteristic parameter $|\partial\cos\varphi/\partial\sigma_1|$:

$$\left|\frac{\partial\cos\varphi}{\partial\sigma_1}\right| = \frac{1}{\sqrt{1+\mu^2}} \frac{\left(\cos\varphi\sqrt{1+\mu^2} - \mu\right)^2}{2\mu\sigma_3 + \frac{2K_{IC}}{\sqrt{\pi c}}} \tag{6}$$

When $\sigma_1=0$, the following is obtained:

$$\left|\frac{\partial\cos\varphi}{\partial\sigma_1}\right| = \frac{2}{\sigma_c^2\sqrt{1+\mu^2}} \frac{K_{IC}}{\sqrt{\pi c}} \tag{7}$$

Since the rock failure characteristic parameter $|\partial\cos\varphi/\partial\sigma_1|$ is invariant, the formulas (6) and (7) are equivalent. Therefore, solving the formulas (6) and (7) simultaneously yields the calculation formula for triaxial compressive strength of rock:

$$\sigma_1 = \sigma_3 + \sqrt{\frac{\mu\sigma_c\sqrt{\pi c}}{K_{IC}}\sigma_c\sigma_3 + \sigma_c^2} \tag{8}$$

The mean indentation crack length and the rock plane-strain fracture toughness in the formula (8) can be determined based on a rock nano-indentation experiment, which represent two controlling parameters of rock mechanical response at the microscale.

SUMMARY

The present application aims to address the scarcity of formation core samples and the high economic cost and time consumption associated with conventional methods for evaluating rock compressive strength, thereby solving the challenge of efficiently and cost-effectively evaluating formation rock compressive strength. For this purpose, the present application proposes a method for evaluating rock compressive strength based on cuttings mineral composition, nano-indentation, and friction tests.

The present application adopts the following technical solutions. A method for evaluating rock compressive strength based on cuttings mineral composition, nano-indentation, and friction tests includes the following steps:

step 1.1: collecting fresh cuttings from a studied formation to prepare dry rock powder samples with a particle size of less than 75 μm, and determining rock mineral composition and relative content of each rock mineral by using an X-ray diffractometer;

step 1.2: collecting fresh cuttings from the studied formation, selecting blocky cuttings with a longest axis particle size of 0.8-1.2 cm, and grinding and polishing the blocky cuttings to prepare rock nano-indentation specimens; performing experiments on the rock nano-indentation specimens using a nano-indenter to obtain nano-indentation load-displacement curves of each rock mineral; observing residual nano-indentation impressions using a metallographic optical microscope, measuring nano-indentation crack lengths of rock, and calculating a mean nano-indentation crack length of rock;

step 1.3: based on the nano-indentation load-displacement curves of each rock mineral, calculating elastic modulus and plane-strain fracture toughness of each rock mineral;

step 1.4: based on the relative content of each rock mineral, the mean nano-indentation crack length of rock, and the plane-strain fracture toughness of each rock mineral, calculating a rock fracture toughness characteristic parameter by integrating parameters of each mineral according to a proportion of each mineral using a weighted superposition method;

step 1.5: collecting fresh cuttings from the studied formation and performing cuttings friction testing to obtain a rock friction coefficient; and step 1.6: based on the rock fracture toughness characteristic parameter and the rock friction coefficient, calculating the rock compressive strength according to a rock strength calculation model.

Further, the specific procedures of the step 1.1 are as follows:

step 1.1.1: collecting fresh cuttings from the studied formation, crushing the cuttings into particles with a size of less than 2 mm using a mortar, taking 5 g of crushed particles, and grinding the particles using an agate mortar to obtain rock powder samples with a particle size of less than 75 m; placing the ground rock powder samples in an oven and drying at 105±5° C. for 4 hours to remove moisture, thereby obtaining dried rock powder samples;

step 1.1.2: weighing approximately 0.5 g of the dried rock powder samples and pouring the samples into a glass sample holder; leveling the samples with a spatula and pressing the samples onto the glass sample holder using a glass plate to ensure tight adherence, thereby obtaining X-ray diffraction specimens; and step 1.1.3: placing the X-ray diffraction specimens into an X-ray diffractometer for experimentation, recording the variation of diffraction intensity with diffraction angle, generating X-ray diffraction patterns, and analyzing the patterns to determine the rock mineral composition and the relative content of each rock mineral.

Further, the specific procedures of the step 1.2 are as follows:

step 1.2.1: collecting fresh cuttings from the studied formation, visually selecting cuttings without obvious fissures, and choosing blocky cuttings with a longest axis particle size of 0.8-1.2 cm; grinding and flattening upper and lower end surfaces to obtain cuttings specimens with flat upper and lower end surfaces;

step 1.2.2: sequentially polishing the upper end surfaces of the cuttings specimens with flat upper and lower end surfaces using polished silk, 1 μm diamond suspension, and 0.05 μm oil-based oxide polishing suspension, thereby obtaining rock nano-indentation specimens with an upper end surface roughness of ≤10 nm;

step 1.2.3: placing the rock nano-indentation specimens into a nano-indenter, and performing indentation experiments on each rock mineral on the upper end surface of the rock nano-indentation specimen at a constant loading rate of 10 mN/s; when a maximum indentation load reaches 200 mN, maintaining the 200 mN load for 15 s, then unloading at a constant rate of 10 mN/s; recording the load and indentation depth during the experiment, and plotting nano-indentation load-displacement curves of each rock mineral; and step 1.2.4: observing indentation impressions of the rock nano-indentation specimens using a metallographic optical microscope, selecting residual impressions with clear indentation cracks, measuring the nano-indentation crack length of rock in each residual impression, and calculating the mean nano-indentation crack length of rock according to the following formula:

$$c = \frac{\sum_{1}^{k} l_j}{k}$$

where c represents the mean nano-indentation crack length of rock, in μm; k represents a total number of indentation cracks, which is an integer; $l_j$ represents a length of a j-th crack, in μm.

Further, the specific procedures of the step 1.3 are as follows:

step 1.3.1: based on the nano-indentation load-displacement curves of each rock mineral, calculating the elastic modulus of each rock mineral according to the following formula:

$$E_{(i)} = \frac{\sqrt{\pi} S}{2\alpha\sqrt{A_c}}$$

where $E_{(i)}$ represents elastic modulus of an i-th rock mineral, in GPa; π represents pi, dimensionless; S represents contact stiffness between an indenter in the rock nano-indentation experiment and the rock nano-indentation specimen, in mN/nm, which equals to a slope of an initial unloading segment of the nano-indentation load-displacement curves; a represents a geometric constant of the indenter, dimensionless; $A_c$ represents the contact area between the indenter in the rock nano-indentation experiment and the rock nano-indentation specimen, in μm²;

step 1.3.2: fitting the nano-indentation load-displacement curves of each rock mineral to obtain power-law equations of the nano-indentation load-displacement curves of each rock mineral during the loading and unloading stages, expressed as follows:

loading stage:

$$P_{l(i)} = P_{max(i)}\left(\frac{h_{(i)}}{h_{l(i)}}\right)^{n_{(i)}}$$

unloading stage:

$$P_{u(i)} = P_{max(i)}\left(\frac{h_{(i)} - h_{f(i)}}{h_{m(i)} - h_{f(i)}}\right)^{m_{(i)}}$$

where $P_{l(i)}$ represents nano-indentation load of the i-th rock mineral during the loading stage, in mN; $P_{max(i)}$ represents a maximum nano-indentation load of the i-th rock mineral, in mN; $h_{(i)}$ represents a nano-indentation depth of the i-th rock mineral, in nm; $h_{l(i)}$ represents a nano-indentation depth of the i-th rock mineral at the moment the maximum load is reached, in nm; $n_{(i)}$ represents power-law exponent of the nano-indentation load-displacement curve for the i-th rock mineral during the loading stage, dimensionless; $P_{u(i)}$ represents nano-indentation load of the i-th rock mineral during the unloading stage, in mN; $h_{f(i)}$ represents a residual nano-indentation depth of the i-th rock mineral, in nm; $h_{m(i)}$ represents a maximum nano-indentation depth of the i-th rock mineral, in nm; $m_{(i)}$ represents power-law exponent of the load-displacement curve for the i-th rock mineral during the unloading stage, dimensionless;

step 1.3.3: based on the power-law equations of the nano-indentation load-displacement curves of each rock mineral during the loading and unloading stages, integrating the loading stage to obtain the total energy and integrating the unloading stage to obtain the elastic energy, thereby calculating the total energy and elastic energy for each rock mineral during the nano-indentation experiment according to the following formulas:

$$U_{t(i)} = \int_0^{h_{m(i)}} P_{l(i)} dh(i) = \int_0^{h_{(i)}} P_{l(i)} dh_{(i)} + \int_{h_{(i)}}^{h_{m(i)}} P_{max(i)} dh_{(i)} = P_{max(i)}\left(h_{m(i)} - \frac{n_{(i)}}{1 + n_{(i)}} h_{l(i)}\right)$$

$$U_{e(i)} = \int_{h_{f(i)}}^{h_{m(i)}} P_{u(i)} dh_{(i)} = \frac{P_{max(i)}(h_{m(i)} - h_{l(i)})}{1 + m_{(i)}}$$

where $U_{t(i)}$ represents the total energy of the i-th rock mineral during the nano-indentation experiment, in mN·μm; $U_{e(i)}$ represents the elastic energy of the i-th rock mineral during the nano-indentation experiment, in mN·μm;

step 1.3.4: based on the total energy for each rock mineral during the nano-indentation experiment, calculating purely plastic energy for each rock mineral during the nano-indentation experiment according to the following formula:

$$U_{pp(i)} = U_{t(i)}\left[1 - \frac{(1 + n_{(i)})(h_{m(i)} - h_{f(i)})}{(1 + m_{(i)})(h_{m(i)} + n_{(i)} h_{m(i)} - n_{(i)} h_{l(i)})}\right] = P_{max(i)}\left(h_{m(i)} - \frac{n_{(i)}}{1 + n_{(i)}} h_{l(i)}\right)\left[1 - \frac{(1 + n_{(i)})(h_{m(i)} - h_{f(i)})}{(1 + m_{(i)})(h_{m(i)} + n_{(i)} h_{m(i)} - n_{(i)} h_{l(i)})}\right]$$

where $U_{pp(i)}$ represents the purely plastic energy of the i-th rock mineral during the nano-indentation experiment, in mN·μm;

step 1.3.5: based on the total energy, the elastic energy, and the purely plastic energy for each rock mineral during the nano-indentation experiment, calculating the fracture energy for each rock mineral during the nano-indentation experiment according to the following formula:

$$U_{c(i)} = U_{t(i)} - U_{e(i)} - U_{pp(i)} = P_{max(i)}\left[\frac{(1+n_{(i)})(h_{m(i)}^2 - h_{f(i)}h_{m(i)}) - n_{(i)}h_{l(i)}(h_{m(i)} - h_{f(i)})}{(1+m_{(i)})(h_{m(i)} + n_{(i)}h_{m(i)} - n_{(i)}h_{l(i)})} - \frac{h_{m(i)} - h_{l(i)}}{1+m_{(i)}}\right] \quad (1)$$

where $U_{c(i)}$ represents the fracture energy of the i-th rock mineral during the nano-indentation experiment, in mN·μm;

step 1.3.6: based on the fracture energy for each rock mineral during the nano-indentation experiment, the elastic modulus of each rock mineral, and the contact area between the indenter in the rock nano-indentation experiment and the rock nano-indentation specimen, calculating plane-strain fracture toughness of each rock mineral according to the following formula:

$$K_{IC(i)} = \sqrt{\frac{U_{c(i)}E_{(i)}}{A_c}}$$

where $K_{IC(i)}$ represents the plane-strain fracture toughness of the i-th rock mineral, in MPa·m$^{0.5}$.

Further, in the step 1.4, the rock fracture toughness characteristic parameter is calculated according to the following formula:

$$K_{CS} = \sum_{1}^{r} f_i \frac{K_{IC(i)}}{\sqrt{\pi c}}$$

where $K_{CS}$ represents the rock fracture toughness characteristic parameter, in MPa, which is an equivalent parameter obtained by weighted integration of the plane-strain fracture toughness of each rock mineral; r represents the number of rock mineral types, which is an integer; $f_i$ represents the relative content of the i-th mineral, in %; and π represents pi, dimensionless.

Further, the specific procedures of the step 1.5 are as follows:

step 1.5.1: collecting fresh cuttings from the studied formation, selecting blocky cuttings with the longest axis particle size of 0.8-1.2 cm, and grinding the testing surface of the blocky cuttings to obtain a flat-surfaced cuttings specimen for friction testing;

step 1.5.2: fixing the cuttings specimen for friction testing onto a fixture of a friction and wear testing machine, performing the friction test on the cuttings under experimental conditions of a normal force of 10 N and a sliding speed of 0.1 mm/s, and recording friction force and normal force data; and step 1.5.3: calculating the friction coefficient based on the recorded friction force and normal force data from the cuttings friction testing according to the following formula:

$$\mu = \frac{F_f}{F_n}$$

where μ represents the rock friction coefficient, dimensionless; $F_f$ represents the friction force, in N; and $F_n$ represents the normal force, in N.

Further, the specific procedures of the step 1.6 are as follows:

step 1.6.1: based on the rock fracture toughness characteristic parameter and the rock friction coefficient, calculating uniaxial compressive strength of rock according to the following formula:

$$\sigma_c = K_{CS}\left[\frac{\sqrt{3}}{\sqrt{1+\mu^2} - \mu}\right]$$

where $\sigma_c$, represents the uniaxial compressive strength of rock, in MPa; μ represents the rock friction coefficient, dimensionless;

step 1.6.2: based on the rock friction coefficient, the rock fracture toughness characteristic parameter, and the uniaxial compressive strength of rock, calculating triaxial compressive strength of rock according to the following formula:

$$\sigma = \sigma_p + \sqrt{\frac{\mu\sigma_c}{K_{CS}}\sigma_c\sigma_p + \sigma_c^2}$$

where $\sigma_p$ represents a confining pressure, in MPa; σ represents the triaxial compressive strength of rock under the confining pressure of $\sigma_p$, in MPa.

In summary, with the adoption of the above technical solution, the present application has the following the beneficial effects:

1. Based on micro-fracture mechanics theory of rock, the present application quantitatively evaluates the nano-indentation microcrack length of rock and the characteristics of load-displacement curves by describing the extension behavior of nano-indentation microcrack, and thereby uses the mechanical behavior of rock micro-fracture as a basis for determining rock compressive strength. The rock compressive strength evaluation method established thereby originates from the microscopic essence of rock structural failure. Compared with conventional methods based on rock strength criteria, the present application not only has a clearer physical meaning but also can more accurately predict rock failure behavior and strength characteristics.

2. The present application obtains the parameters required for the evaluation method for rock compressive strength by using cuttings mineral composition, nano-indentation, and friction tests, thereby implementing rock compressive strength evaluation. The present application effectively overcomes the difficulty of evaluating rock compressive strength when formation core samples are scarce and significantly reduces the economic and time costs associated with conventional core-based testing methods. Therefore, the present application provides an effective technical means for evaluating rock compressive strength in rock mass engineering, especially in cases where petroleum engineering cores are difficult to obtain.

BRIEF DESCRIPTION OF DRAWINGS

FIG. 1 is a flow chart of a method for evaluating rock compressive strength based on cuttings mineral composition, nano-indentation, and friction tests;

FIG. 2 is a diagram of mineral composition and relative content of each mineral in the Qiongzhusi Formation shale and Dengying Formation dolostone from Well PS6;

FIG. 3 is an image of a nano-indentation specimen after grinding and polishing;

FIG. 4 is a diagram of load-displacement curves of nano-indentation for each rock;

FIG. 6 is a diagram of power-law equations of nano-indentation load-displacement curves for minerals of Qiongzhusi Formation shale and Dengying Formation dolostone from Well PS6 and parameters for calculating rock compressive strength;

DESCRIPTION OF EMBODIMENTS

Figure 5:
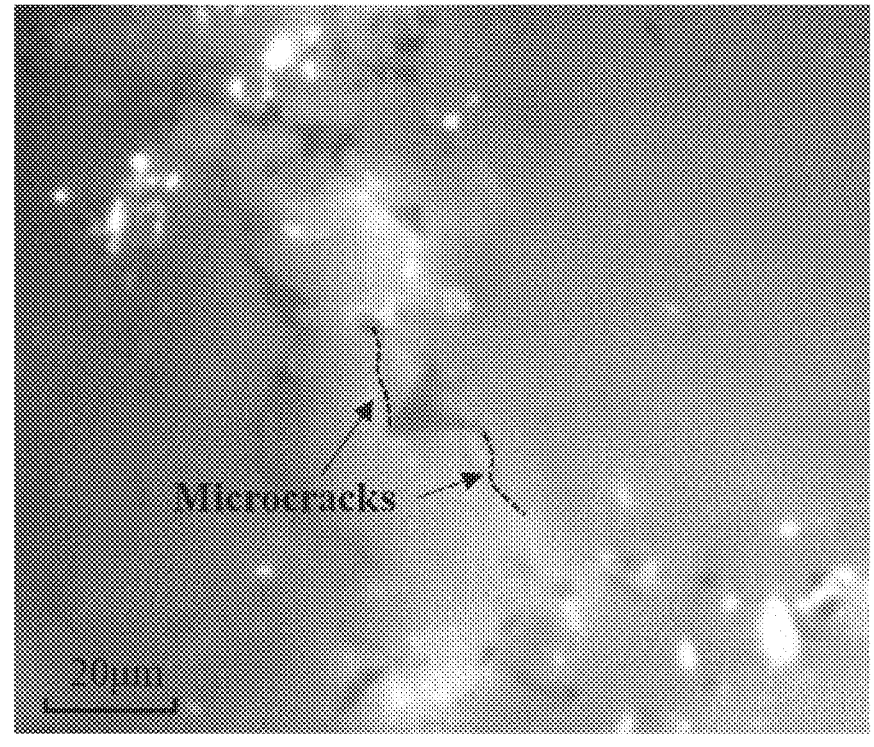
FIG. 5 is a diagram showing measurement of nano-indentation crack lengths of rock in residual nano-indentation impressions.

To make the objectives, technical solutions, and advantages of the present application more clearly understood, the present application is further illustrated below in conjunction with the accompanying drawings and embodiments. It should be understood that the specific embodiments described herein are provided only to explain the present application and are not intended to limit the present application.

A flow chart of a method for evaluating rock compressive strength based on cuttings mineral composition, nano-indentation, and friction tests, as implemented in the present application, is shown in FIG. 1, and is described in detail as follows:

1. Fresh cuttings from a studied formation are collected to prepare dry rock powder samples with a particle size of less than 75 μm, and rock mineral composition and relative content of each rock mineral are determined by using an X-ray diffractometer. The specific procedures are as follows:

(1) Fresh cuttings from the studied formation are collected and crushed in a mortar to particles with a size of less than 2 mm. 5 g of the crushed particles are taken and ground in an agate mortar to obtain rock powder specimens with a particle size of less than 75 μm, thereby ensuring sample homogeneity and testing accuracy. The ground rock powder specimens are placed in an oven and dried at 105±5° C. for 4 hours to remove moisture, and the dried rock powder specimens are obtained.

(2) Approximately 0.5 g of the dried rock powder specimens is weighed and poured into a glass sample holder. The powder specimens are leveled with a spatula and pressed with a glass plate to fit tightly against the glass sample holder, ensuring that the sample surface is flush with the holder surface and avoiding protrusions or depressions, thereby preparing X-ray diffraction test specimens.

(3) The X-ray diffractometer is preheated to ensure stable instrument performance. The X-ray diffraction test specimens are placed in the X-ray diffractometer, the testing program is started to scan the specimens, the diffraction intensity versus diffraction angle is recorded, and an X-ray diffraction pattern is generated to analyze and obtain the rock mineral composition and the relative content of each rock mineral.

2. Fresh cuttings from the studied formation are collected, blocky cuttings with a longest axis particle size of 0.8-1.2 cm are selected, and the blocky cuttings are ground and polished to prepare rock nano-indentation specimens. Experiments are performed on the rock nano-indentation specimens using a nano-indenter to obtain nano-indentation load-displacement curves of each rock mineral. Residual nano-indentation impressions are observed using a metallographic optical microscope, nano-indentation crack lengths of rock are measured, and a mean nano-indentation crack length of rock is calculated. The specific procedures are as follows:

(1) Fresh cuttings from the studied formation are collected and visually inspected to select cuttings without obvious fractures and with uniform texture. Blocky cuttings with a longest-axis particle size of 0.8-1.2 cm are selected, and the upper and lower end surfaces are sequentially ground with metallographic sandpapers of 400-800 grit to achieve flat upper and lower end surfaces, obtaining cuttings specimens with flat end surfaces.

(2) The upper end surface of the cuttings specimens with flat upper and lower end surfaces is polished using polishing silk, followed by further grinding with 1 μm diamond suspension and fine polishing with 0.05 μm oil-based oxide polishing suspension. This stepwise reduction in abrasive particle size achieves surface polishing of the upper end surface of the cuttings specimens with flat upper and lower end surfaces, resulting in rock nano-indentation specimens with an upper end surface roughness of ≤10 nm.

(3) The rock nano-indentation specimens are placed in a nano-indenter, and indentation experiments are performed on each rock mineral on the upper end surface of the specimens at a constant loading rate of 10 mN/s. When the maximum indentation load reaches 200 mN, the load is held for 15 s. The specimens are then unloaded at a constant unloading rate of 10 mN/s, and the load and indentation depth throughout the experiment are recorded. Based on these data, nano-indentation load-displacement curves of each rock mineral are plotted.

(4) The indentation impressions of the rock nano-indentation specimens are observed using a metallographic optical microscope. Residual nano-indentation impressions with clear indentation cracks are selected, and the nano-indentation crack lengths of each residual impression are measured using the microscope's built-in measurement tool. The mean nano-indentation crack length of the rock is calculated using the following formula:

$$c = \frac{\sum_{1}^{k} l_j}{k} \tag{9}$$

where c represents the mean nano-indentation crack length of rock, in μm; k represents a total number of indentation cracks, which is an integer; $l_j$ represents a length of a j-th crack, in μm.

3. The elastic modulus and plane-strain fracture toughness of each rock mineral are calculated based on the nano-indentation load-displacement curves of each rock mineral. The specific procedures are as follows:

(1) The elastic modulus of each rock mineral is calculated based on the nano-indentation load-displacement curves of each rock mineral in combination with the intrinsic parameters of the nano-indenter. The calculation formula is as follows:

$$E_{(i)} = \frac{\sqrt{\pi}S}{2\alpha\sqrt{A_c}} \tag{10}$$

where $E_{(i)}$ represents elastic modulus of an i-th rock mineral, in GPa; π represents pi, dimensionless; S represents contact stiffness between an indenter in the rock nano-indentation experiment and the rock nano-indentation specimen, in mN/nm, which equals to a slope of an initial unloading segment of the nano-indentation load-displacement curves; α represents a geometric constant of the indenter, dimensionless; $A_c$ represents the contact area between the indenter in the rock nano-indentation experiment and the rock nano-indentation specimen, in $\mu m^2$.

(2) The nano-indentation load-displacement curves of each rock mineral are fitted, and a power-law model is applied to the curve data of each rock mineral for the loading and unloading stages, respectively. Parameters are optimized using the least-squares method to obtain power-law equations of the nano-indentation load-displacement curves of each rock mineral for the loading and unloading stages. The expressions are as follows:

loading stage:

$$P_{1(i)} = P_{max(i)}\left(\frac{h_{(i)}}{h_{l(i)}}\right)^{n(i)} \tag{11}$$

unloading stage:

$$P_{u(i)} = P_{max(i)}\left(\frac{h_{(i)} - h_{f(i)}}{h_{m(i)} - h_{f(i)}}\right)^{m(i)} \tag{12}$$

where $P_{l(i)}$ represents nano-indentation load of the i-th rock mineral during the loading stage, in mN; $P_{max(i)}$ represents a maximum nano-indentation load of the i-th rock mineral, in mN; $h_{(i)}$ represents a nano-indentation depth of the i-th rock mineral, in nm; $h_{l(i)}$ represents a nano-indentation depth of the i-th rock mineral at the moment the maximum load is reached, in nm; $n_{(i)}$ represents power-law exponent of the nano-indentation load-displacement curve for the i-th rock mineral during the loading stage, dimensionless; $P_{u(i)}$ represents the nano-indentation load of the i-th rock mineral during the unloading stage, in mN; $h_{f(i)}$ represents a residual nano-indentation depth of the i-th rock mineral, in nm; $h_{m(i)}$ represents a maximum nano-indentation depth of the i-th rock mineral, in nm; $m_{(i)}$ represents power-law exponent of the load-displacement curve for the i-th rock mineral during the unloading stage, dimensionless.

(3) Based on the power-law equations of the nano-indentation load-displacement curves of each rock mineral for the loading and unloading stages, the total energy is obtained by integrating the loading stage, and the elastic energy is obtained by integrating the unloading stage. The total energy and elastic energy during the nano-indentation experiment for each rock mineral are thus calculated using the following formulas:

$$U_{t(i)} = \int_0^{h_{m(i)}} P_{l(i)}dh(i) = \int_0^{h_{(i)}} P_{l(i)}dh_{(i)} + \int_{h_{l(i)}}^{h_{m(i)}} P_{max(i)}dh_{(i)} = P_{max(i)}\left(h_{m(i)} - \frac{n_{(i)}}{1+n_{(i)}}h_{l(i)}\right) \tag{13}$$

$$U_{e(i)} = \int_{h_{f(i)}}^{h_{m(i)}} P_{u(i)}dh_{(i)} = \frac{P_{max(i)}(h_{m(i)} - h_{l(i)})}{1+m_{(i)}} \tag{14}$$

where $U_{t(i)}$ represents the total energy of the i-th rock mineral during the nano-indentation experiment, in mN·μm; $U_{e(i)}$ represents the elastic energy of the i-th rock mineral during the nano-indentation experiment, in mN·μm.

(4) Based on the total energy during the nano-indentation experiment for each rock mineral, the purely plastic energy for each rock mineral during the nano-indentation experiment is calculated using the following formula:

$$U_{pp(i)} = U_{t(i)}\left[1 - \frac{(1+n_{(i)})(h_{m(i)} - h_{f(i)})}{(1+m_{(i)})(h_{m(i)} + n_{(i)}h_{m(i)} - n_{(i)}h_{1(i)})}\right] = P_{max(i)}\left(h_{m(i)} - \frac{n_{(i)}}{1+n_{(i)}}h_{l(i)}\right)\left[1 - \frac{(1+n_{(i)})(h_{m(i)} - h_{f(i)})}{(1+m_{(i)})(h_{m(i)} + n_{(i)}h_{m(i)} - n_{(i)}h_{l(i)})}\right] \tag{15}$$

where $U_{pp(i)}$ represents the purely plastic energy of the i-th rock mineral during the nano-indentation experiment, in mN m.

(5) Based on the total energy, the elastic energy, and the purely plastic energy for each rock mineral during the nano-indentation experiment, the fracture energy during the nano-indentation experiment of each rock mineral is calculated according to the energy balance principle by subtracting the sum of the elastic energy and purely plastic energy from the total energy. The calculation formula is as follows:

$$U_{c(i)} = U_{t(i)} - U_{e(i)} - U_{pp(i)} = P_{max(i)}\left[\frac{(1+n_{(i)})(h_{m(i)}^2 - h_{f(i)}h_{m(i)}) - n_{(i)}h_{l(i)}(h_{m(i)} - h_{f(i)})}{(1+m_{(i)})(h_{m(i)} + n_{(i)}h_{m(i)} - n_{i,)}h_{l(i)})} - \frac{h_{m(i)} - h_{l(i)}}{1+m_{(i)}}\right] \tag{16}$$

where $U_{c(i)}$ represents the fracture energy of the i-th rock mineral during the nano-indentation experiment, in mN m.

(6) Based on the fracture energy for each rock mineral during the nano-indentation experiment, the elastic modulus of each rock mineral, and the contact area between the contact area between the indenter in the rock nano-indentation experiment and the rock nano-indentation specimen, the plane-strain fracture toughness of each rock mineral is calculated using the following formula:

$$K_{IC(i)} = \sqrt{\frac{U_{c(i)}E_{(i)}}{A_c}} \tag{17}$$

where $K_{IC(i)}$ represents the plane-strain fracture toughness of the i-th rock mineral, in MPa·m0.5.

4. Based on the relative content of each rock mineral, the mean nano-indentation crack length of the rock, and the plane-strain fracture toughness of each rock mineral, the rock fracture toughness characteristic parameter is obtained by integrating the parameters of each mineral according to the proportion of each mineral using a weighted superposition method. The calculation formula is as follows:

$$K_{CS} = \sum_{1}^{r} f_i \frac{K_{IC(i)}}{\sqrt{\pi c}} \tag{18}$$

where $K_{CS}$ represents the rock fracture toughness characteristic parameter, in MPa, which is an equivalent parameter obtained by weighted integration of the plane-strain fracture toughness of each rock mineral; r represents the number of rock mineral types, which is an integer; $f_i$ represents the relative content of the i-th mineral, in %; and π represents pi, dimensionless.

5. Fresh cuttings from the studied formation are collected, and cuttings friction testing is performed to obtain a rock friction coefficient. The specific procedures are as follows:

(1) Fresh cuttings of the studied formation are collected, and blocky cuttings with a longest-axis particle size of 0.8-1.2 cm are selected. The testing surface of the blocky cuttings is progressively ground with sandpaper to remove surface protrusions and impurities until smooth and flat, thereby obtaining a flat-surfaced cuttings specimen for friction testing.

(2) The cuttings specimen for friction testing is fixed on the fixture of a friction and wear testing machine. Experimental parameters are set with a normal force of 10 N and a sliding speed of 0.1 mm/s. The friction and wear testing machine is operated to perform the cuttings friction experiment, and the friction force and normal force data are recorded in real time during the experiment.

(3) Based on the recorded friction force and normal force data from the cuttings friction testing, the friction coefficient is calculated using the following formula:

$$\mu = \frac{F_f}{F_n} \tag{19}$$

where μ represents the rock friction coefficient, dimensionless; $F_f$ represents the friction force, in N; and $F_n$ represents the normal force, in N.

6. Based on the rock fracture toughness characteristic parameter and the rock friction coefficient, the rock compressive strength is calculated according to a rock strength calculation model. The specific procedures are as follows:

(1) Based on the rock fracture toughness characteristic parameter and the rock friction coefficient, uniaxial compressive strength of rock is calculated according to the following formula:

$$\sigma_c = K_{CS}\left[\frac{\sqrt{3}}{\sqrt{1+\mu^2}-\mu}\right] \tag{20}$$

where $\sigma_c$ represents the uniaxial compressive strength of rock, in MPa.

(2) Based on the rock friction coefficient, the rock fracture toughness characteristic parameter, and the uniaxial compressive strength of rock, the rock compressive strength calculation model is obtained by combining formula (8) and formula (18), as shown in formula (21). The rock compressive strength is calculated using this model:

$$\sigma = \sigma_p + \sqrt{\frac{\mu\sigma_c}{K_{CS}}\sigma_c\sigma_p + \sigma_c^2} \tag{21}$$

where $\sigma_p$ represents a confining pressure, in MPa; σ represents the triaxial compressive strength of rock under the confining pressure of $\sigma_p$, in MPa.

EMBODIMENT

This embodiment evaluates compressive strength of rocks from the Qiongzhusi Formation and the Dengying Formation in a certain well area of the Sichuan Basin, with cuttings specimens collected from Well PS6 in the well area. The specific steps were as follows:

Step 1: Fresh shale cuttings from the 7655-7700 m section of the Qiongzhusi Formation and fresh dolostone cuttings from the 7990-8010 m section of the Dengying Formation of Well PS6 are collected, and the cuttings are crushed into particles with a particle size less than 2 mm by using a mortar. Approximately 5 g of the crushed particles are taken, and ground with an agate mortar to obtain dry rock powder samples with a particle size less than 75 μm. The ground dry rock powder samples are placed in an oven and dried at 105±5° C. for 4 hours to remove moisture, thereby obtaining dried rock powder samples. Approximately 0.5 g of dried rock powder sample is weighed and poured into a glass sample holder. The powder sample is leveled with a spatula and pressed with a glass plate to ensure tight contact with the glass sample holder, thereby preparing an X-ray diffraction specimen. An X-ray diffractometer is turned on and preheated. The X-ray diffraction specimen is placed in the X-ray diffractometer, and a testing program is started to scan the specimen. The diffraction intensity is recorded as a function of diffraction angle to generate an X-ray diffraction spectrum, whereby rock mineral composition and relative contents of each rock mineral are analyzed. The mineral composition and relative contents of minerals in the shale of the Qiongzhusi Formation and the dolostone of the Dengying Formation from Well PS6 are obtained as shown in FIG. 2.

Step 2: Fresh shale cuttings from the 7655-7700 m section of the Qiongzhusi Formation and fresh dolostone cuttings from the 7990-8010 m section of the Dengying Formation of Well PS6 are collected. Cuttings specimens without obvious fractures and with uniform texture are visually selected. Blocky cuttings with a longest axis particle size of 0.8-1.2 cm are selected and sequentially ground on the upper and lower end surfaces using metallographic sandpaper of 400-800 grit until flat. The upper end surface is successively polished with polishing silk, 1 μm diamond suspension, and 0.05 μm oil-based oxide polishing suspension to obtain a rock nano-indentation specimen with an upper end surface roughness≤10 nm. The rock nano-indentation specimens after grinding and polishing are shown in FIG. 3. The ground and polished rock nano-indentation specimens of the Qiongzhusi Formation and the Dengying Formation from Well PS6 are placed in a nano-indenter, and nano-indentation experiments are performed on each rock mineral on the upper end surface of rock nano-indentation specimens at a constant loading rate of 10 mN/s, with loading continued until a maximum indentation load of 200 mN is reached and held for 15 s. The specimens are then unloaded at a constant unloading rate of 10 mN/s, the real-time load and indentation depth data are precisely recorded throughout, and nano-indentation load-displacement curves of each rock mineral are plotted. The nano-indentation load-displacement curves of each rock mineral are shown in FIG. 4. The indentation impressions on the nano-indentation specimens are observed with a metallographic optical microscope, and residual impressions with clear indentation cracks are selected. The nano-indentation crack lengths of rock in each residual impression are measured using the microscope's built-in measurement tool. The measurements of nano-indentation crack lengths of rock in residual nano-indentation impressions are shown in FIG. 5. A mean nano-indentation crack length of rock is calculated by using formula (9).

Figure 7:
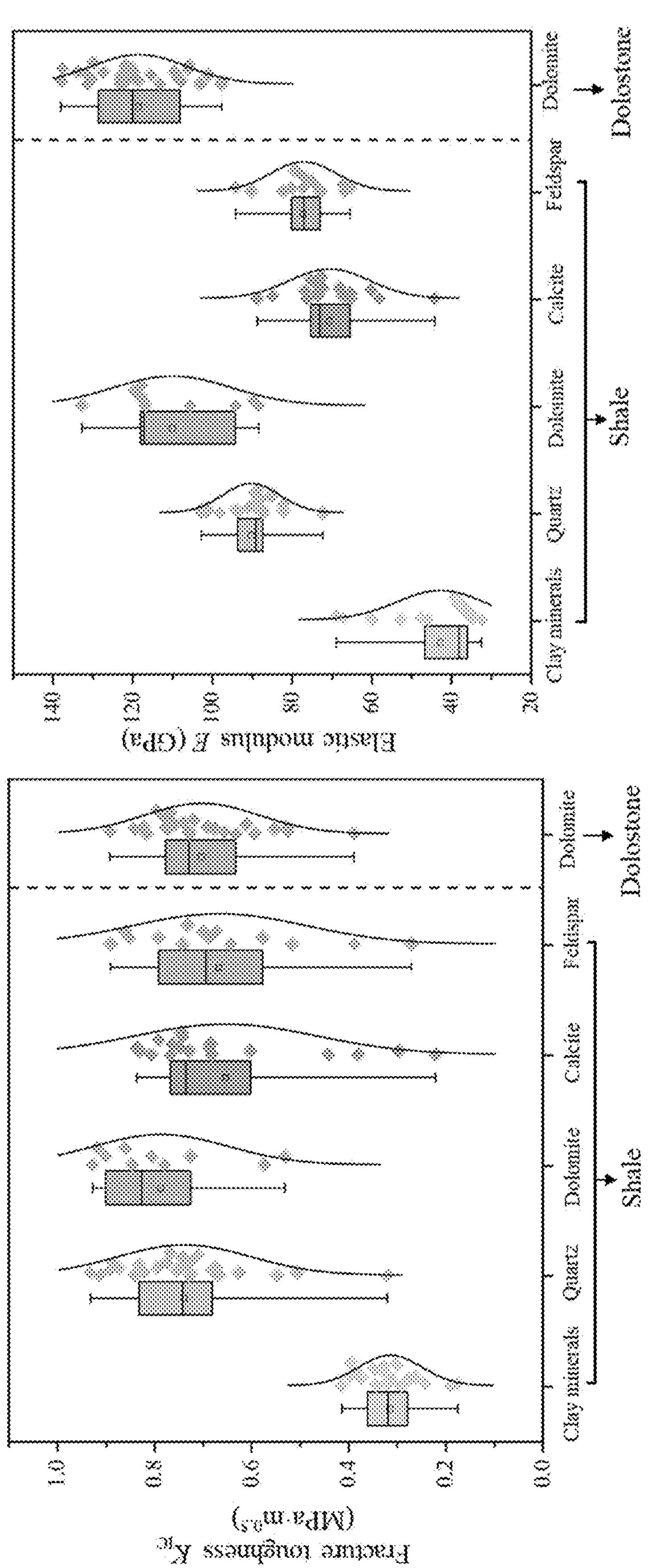
FIG. 7 is a statistical result diagram of plane-strain fracture toughness and elastic modulus of each rock mineral.

Step 3: Based on the nano-indentation load-displacement curves of each rock mineral obtained from the shale of the Qiongzhusi Formation and the dolostone of the Dengying Formation from Well PS6 and the fundamental parameters shown in FIG. 6, a geometric constant of 1.034 for the indenter in the rock nano-indentation experiment is used, and elastic modulus of each rock mineral is calculated by using formula (10). The statistical results of elastic modulus of each rock mineral are shown in FIG. 7. The nano-indentation load-displacement curves of each rock mineral are fitted to obtain power-law equations of the nano-indentation load-displacement curves of each rock mineral during the loading and unloading stages, as shown in FIG. 6. Because contents of clay minerals, quartz, calcite, and feldspar in dolostone of the Dengying Formation from Well PS6 are all less than 1%, and dolomite content is 98.3% (see FIG. 2), only dolomite is considered in the dolomite strength evaluation in this embodiment. Based on the power-law equations of the nano-indentation load-displacement curves of each rock mineral, the total energy and elastic energy during the nano-indentation experiments of each rock mineral are calculated by using formulas (13) and (14). Based on the total energy during the nano-indentation experiments of each rock mineral, purely plastic energy for each rock mineral during the nano-indentation experiments is calculated by using formula (15). Based on the total energy, the elastic energy, and the purely plastic energy of each rock mineral during the nano-indentation experiment, the fracture energy for each rock mineral during the nano-indentation experiment is calculated by using formula (16). Based on the fracture energy for each rock mineral during the nano-indentation experiment, the elastic modulus of each rock mineral, and the contact area between the contact area between the indenter in the rock nano-indentation experiment and the rock nano-indentation specimen, the plane-strain fracture toughness of each rock mineral is calculated by using formula (17). The statistical results of the plane-strain fracture toughness of each rock mineral are shown in FIG. 7.

Step 4: Based on the relative content of each rock mineral, the mean nano-indentation crack length of the rock, and the plane-strain fracture toughness of each rock mineral, the rock failure characteristic parameters are calculated by using formula (18).

Figure 8:
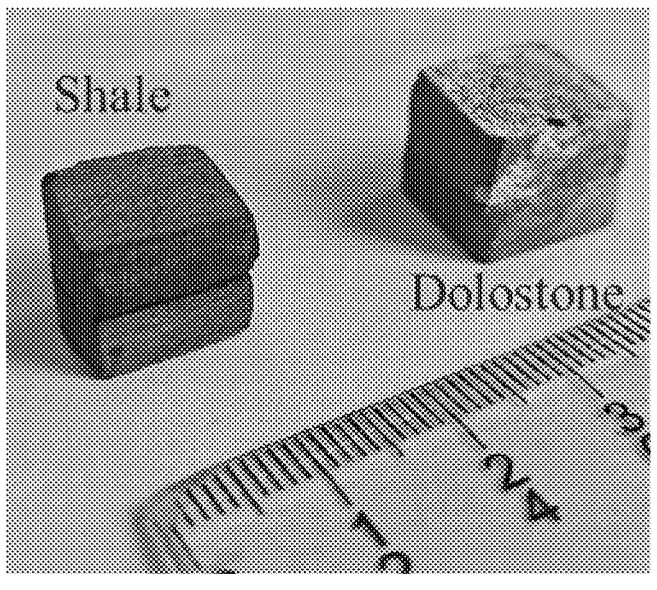
FIG. 8 is an image of a flat-surfaced cuttings specimen after grinding for friction testing.

Step 5: Fresh shale cuttings from the 7655-7700 m section of the Qiongzhusi Formation and fresh dolostone cuttings from the 7990-8010 m section of the Dengying Formation of Well PS6 are collected. Blocky cuttings with a longest axis particle size of 0.8-1.2 cm are selected and sequentially ground on the test surface with sandpaper to remove surface protrusions and impurities until flat and smooth, thereby obtaining a flat-surfaced cuttings specimen for friction testing, as shown in FIG. 8. The cuttings specimen for friction testing is fixed on the fixture of a friction and wear testing machine. Experimental parameters are set with a normal force of 10 N and a sliding speed of 0.1 mm/s. The friction and wear testing machine is operated to perform the cuttings friction experiment, and the friction force and normal force data are recorded in real time during the experiment. The rock friction coefficient is calculated by using formula (19).

Figure 9:
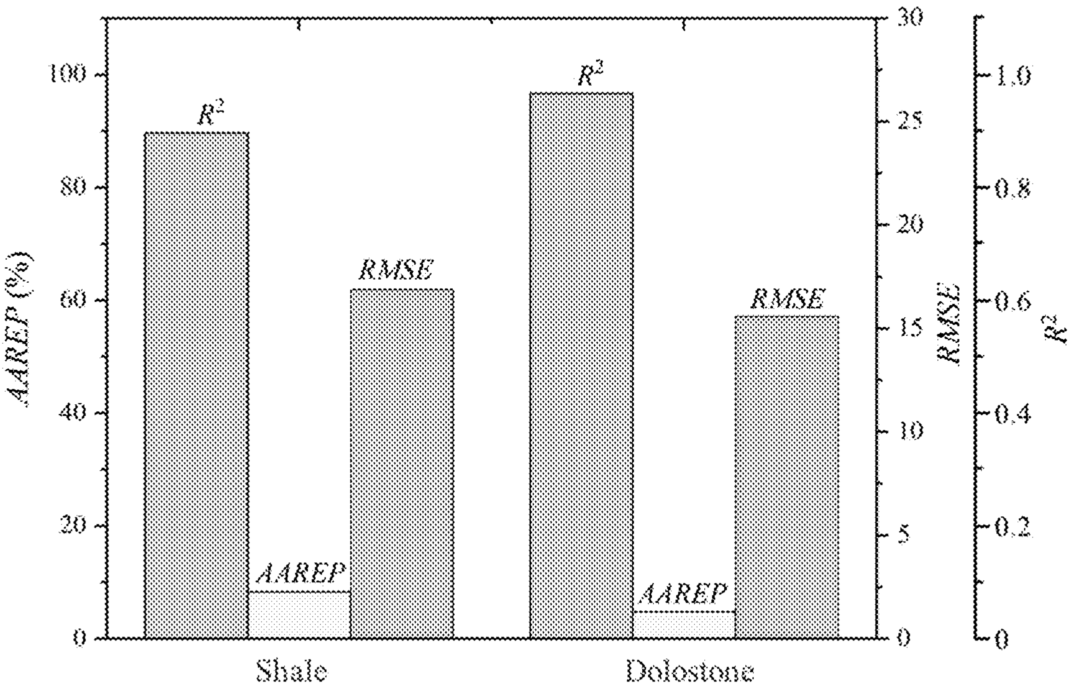
FIG. 9 is an error analysis diagram of rock compressive strength evaluation results.

Step 6: Based on the rock failure characteristic parameters and the rock friction coefficient, uniaxial compressive strength of the rock is calculated by using formula (20). Based on the rock friction coefficient, the rock failure characteristic parameters, and the rock uniaxial compressive strength, triaxial compressive strength of the rock is calculated by using formula (21). The comparison between the rock compressive strength calculated by the method of the present application and the results of triaxial compression experiments is shown in FIG. 9. It can be seen from FIG. 9 that the coefficient of determination $R^2$, average absolute relative error percentage (AAREP), and root mean square error (RMSE) of shale compressive strength calculated by the method of the present application are 0.8967, 8.28%, and 16.89, respectively; the $R^2$, AAREP, and RMSE of dolostone compressive strength are 0.9659, 4.77%, and 15.57, respectively, which indicates high accuracy of rock compressive strength evaluated by the present application.

The above mentioned contents are only preferred embodiments of the present application and are not intended to limit the present application. Any modification, equivalent substitution, improvement and the like made within the spirit and principle of the present application shall all fall within the scope of protection of the present application.

What is claimed is:

1. A method for evaluating rock compressive strength based on cuttings mineral composition, nano-indentation, and friction tests, comprising the following steps:

step 1.1: collecting fresh cuttings from a studied formation to prepare dry rock powder samples with a particle size of less than 75 μm, and determining rock mineral composition and relative content of each rock mineral by using an X-ray diffractometer;

step 1.2: collecting fresh cuttings from the studied formation, selecting blocky cuttings with a longest axis particle size of 0.8-1.2 cm, and grinding and polishing the blocky cuttings to prepare rock nano-indentation specimens; performing experiments on the rock nano-indentation specimens using a nano-indenter to obtain nano-indentation load-displacement curves of each rock mineral; observing residual nano-indentation impressions using a metallographic optical microscope, measuring nano-indentation crack lengths of rock, and calculating a mean nano-indentation crack length of rock;

step 1.3: based on the nano-indentation load-displacement curves of each rock mineral, calculating elastic modulus and plane-strain fracture toughness of each rock mineral;

step 1.4: based on the relative content of each rock mineral, the mean nano-indentation crack length of rock, and the plane-strain fracture toughness of each rock mineral, calculating a rock fracture toughness characteristic parameter by integrating parameters of each mineral according to a proportion of each mineral using a weighted superposition method;

step 1.5: collecting fresh cuttings from the studied formation and performing cuttings friction testing to obtain a rock friction coefficient;

step 1.6: based on the rock fracture toughness characteristic parameter and the rock friction coefficient, calculating the rock compressive strength according to a rock strength calculation model; wherein:

in the step 1.4, the rock fracture toughness characteristic parameter is calculated according to the following formula:

$$K_{CS} = \sum_{1}^{r} f_i \frac{K_{IC(i)}}{\sqrt{\pi c}}$$

wherein $K_{CS}$ represents the rock fracture toughness characteristic parameter, in MPa, which is an equivalent parameter obtained by weighted integration of the plane-strain fracture toughness of each rock mineral; r represents a number of rock mineral types, which is an integer; $f_i$ represents a relative content of an i-th mineral, in %; $K_{IC(i)}$ represents the plane-strain fracture toughness of the i-th rock mineral, in $MPa \cdot m^{0.5}$; π represents pi, dimensionless; c represents the mean nano-indentation crack length of rock, in μm;

the specific procedures of the step 1.6 are as follows:

step 1.6.1: based on the rock fracture toughness characteristic parameter and the rock friction coefficient, calculating uniaxial compressive strength of rock according to the following formula:

$$\sigma_c = K_{CS}\left[\frac{\sqrt{3}}{\sqrt{1+\mu^2}-\mu}\right]$$

wherein $\sigma_c$ represents the uniaxial compressive strength of rock, in MPa; μ represents the rock friction coefficient, dimensionless;

step 1.6.2: based on the rock friction coefficient, the rock fracture toughness characteristic parameter, and the uniaxial compressive strength of rock, calculating triaxial compressive strength of rock according to the following formula:

$$\sigma = \sigma_p + \sqrt{\frac{\mu\sigma_c}{K_{CS}}\sigma_c\sigma_p + \sigma_c^2}$$

wherein $\sigma_p$ represents a confining pressure, in MPa; and σ represents the triaxial compressive strength of rock under the confining pressure of $\sigma_p$, in MPa.

2. The method for evaluating rock compressive strength based on cuttings mineral composition, nano-indentation, and friction tests according to claim 1, wherein the specific procedures of the step 1.1 are as follows:

step 1.1.1: collecting fresh cuttings from the studied formation, crushing the cuttings into particles with a particle size of less than 2 mm using a mortar, taking 5 g of crushed particles, and grinding the particles using an agate mortar to obtain rock powder samples with a particle size of less than 75 μm; placing the ground rock powder samples in an oven and drying at 105±5° C. for 4 hours to remove moisture, thereby obtaining dried rock powder samples;

step 1.1.2: weighing approximately 0.5 g of the dried rock powder samples and pouring the samples into a glass sample holder; leveling the samples with a spatula and pressing the samples onto the glass sample holder using a glass plate to ensure tight adherence, thereby obtaining X-ray diffraction specimens; and step 1.1.3: placing the X-ray diffraction specimens into an X-ray diffractometer for experimentation, recording the variation of diffraction intensity with diffraction angle, generating X-ray diffraction patterns, and analyzing the patterns to determine the rock mineral composition and the relative content of each rock mineral.

3. The method for evaluating rock compressive strength based on cuttings mineral composition, nano-indentation, and friction tests according to claim 1, wherein the specific procedures of the step 1.2 are as follows:

step 1.2.1: collecting fresh cuttings from the studied formation, visually selecting cuttings without obvious fissures, and choosing blocky cuttings with a longest axis particle size of 0.8-1.2 cm; grinding and flattening upper and lower end surfaces to obtain cuttings specimens with flat upper and lower end surfaces;

step 1.2.2: sequentially polishing the upper end surfaces of the cuttings specimens with flat upper and lower end surfaces using polished silk, 1 m diamond suspension, and 0.05 μm oil-based oxide polishing suspension, thereby obtaining rock nano-indentation specimens with an upper end surface roughness of ≤10 nm;

step 1.2.3: placing the rock nano-indentation specimens into a nano-indenter, and performing indentation experiments on each rock mineral on the upper end surface of the rock nano-indentation specimen at a constant loading rate of 10 mN/s; when a maximum indentation load reaches 200 mN, maintaining the 200 mN load for 15 s, then unloading at a constant rate of 10 mN/s; recording the load and indentation depth during the experiment, and plotting nano-indentation load-displacement curves of each rock mineral; and step 1.2.4: observing indentation impressions of the rock nano-indentation specimens using a metallographic optical microscope, selecting residual impressions with clear indentation cracks, measuring the nano-indentation crack length of rock in each residual impression, and calculating the mean nano-indentation crack length of rock according to the following formula:

$$c = \frac{\sum_{1}^{k} l_j}{k}$$

wherein c represents the mean nano-indentation crack length of rock; k represents a total number of indentation cracks, which is an integer; and $l_j$ represents a length of a j-th crack.

4. The method for evaluating rock compressive strength based on cuttings mineral composition, nano-indentation, and friction tests according to claim 1, wherein the specific procedures of the step 1.3 are as follows:

step 1.3.1: based on the nano-indentation load-displacement curves of each rock mineral, calculating the elastic modulus of each rock mineral according to the following formula:

$$E_{(i)} = \frac{\sqrt{\pi}S}{2\alpha\sqrt{A_c}}$$

wherein $E_{(i)}$ represents elastic modulus of an i-th rock mineral, in GPa; π represents pi, dimensionless; S represents contact stiffness between an indenter in a rock nano-indentation experiment and the rock nano-indentation specimen, in mN/nm, which equals to a slope of an initial unloading segment of the nano-indentation load-displacement curves; a represents a geometric constant of the indenter, dimensionless; $A_c$ represents an contact area between the indenter in the rock nano-indentation experiment and the rock nano-indentation specimen, in $\mu m^2$;

step 1.3.2: fitting the nano-indentation load-displacement curves of each rock mineral to obtain power-law equations of the nano-indentation load-displacement curves of each rock mineral during the loading and unloading stages, expressed as follows:

loading stage:

$$P_{1(i)} = P_{max(i)}\left(\frac{h_{(i)}}{h_{1(i)}}\right)^{n(i)}$$

unloading stage:

$$P_{u(i)} = P_{max(i)}\left(\frac{h_{(i)} - h_{f(i)}}{h_{m(i)} - h_{f(i)}}\right)^{m(i)}$$

wherein Pl(i) represents nano-indentation load of the i-th rock mineral during the loading stage, in mN; $P_{max(i)}$ represents a maximum nano-indentation load of the i-th rock mineral, in mN; $h_{(i)}$ represents a nano-indentation depth of the i-th rock mineral, in nm; $h_{l(i)}$ represents a nano-indentation depth of the i-th rock mineral at the moment the maximum load is reached, in nm; $n_{(i)}$ represents the power-law exponent of the nano-indentation load-displacement curve for the i-th rock mineral during the loading stage, dimensionless; $P_{u(i)}$ represents nano-indentation load of the i-th rock mineral during the unloading stage, in mN; $h_{f(i)}$ represents a residual nano-indentation depth of the i-th rock mineral, in nm; $h_{m(i)}$ represents a maximum nano-indentation depth of the i-th rock mineral, in nm; $m_{(i)}$ represents power-law exponent of the load-displacement curve for the i-th rock mineral during the unloading stage, dimensionless;

step 1.3.3: based on the power-law equations of the nano-indentation load-displacement curves of each rock mineral during the loading and unloading stages, integrating the loading stage to obtain total energy and integrating the unloading stage to obtain elastic energy, thereby calculating total energy and elastic energy for each rock mineral during the nano-indentation experiment according to the following formulas:

$$U_{t(i)} = \int_0^{h_{m(i)}} P_{l(i)}dh(i) = \int_0^{h_{l(i)}} P_{l(i)}dh_{(i)} + \int_{h_{l(i)}}^{h_{m(i)}} P_{max(i)}dh_{(i)} = P_{max(i)}\left(h_{m(i)} - \frac{n_{(i)}}{1+n_{(i)}}h_{l(t)}\right)$$

-continued $$U_{e(i)} = \int_0^{h_{m(i)}} p_{u(i)}dh_{(i)} = \frac{P_{max(i)}(h_{m(i)} - h_{l(i)})}{1 - m_{(t)}}$$

wherein $U_{t(i)}$ represents the total energy of the i-th rock mineral during the nano-indentation experiment, in mN·μM; $U_{e(i)}$ represents the elastic energy of the i-th rock mineral during the nano-indentation experiment, in mN·μm;

step 1.3.4: based on the total energy for each rock mineral during the nano-indentation experiment, calculating purely plastic energy for each rock mineral during the nano-indentation experiment according to the following formula:

$$U_{pp(i)} = U_{t(i)}\left[1 - \frac{(1+n_{(i)})(h_{m(i)} - h_{f(i)})}{(1+m_{(i)})(h_{m(i)} + n_{(i)}h_{m(i)} - n_{(i)}h_{l(i)})}\right] = P_{max(i)}\left(h_{m(i)} - \frac{n_{(i)}}{1+n_{(i)}}h_{l(i)}\right)\left[1 - \frac{(1+n_{(i)})(h_{m(i)} - h_{f(i)})}{(1+m_{(i)})(h_{m(i)} + n_{(i)}h_{m(i)} - n_{(i)}h_{l(i)})}\right]$$

wherein $U_{pp(i)}$ represents the purely plastic energy of the i-th rock mineral during the nano-indentation experiment, in mN·μm;

step 1.3.5: based on the total energy, the elastic energy, and the purely plastic energy for each rock mineral during the nano-indentation experiment, calculating fracture energy for each rock mineral during the nano-indentation experiment according to the following formula:

$$U_{pp(i)} = U_{t(i)}\left[1 - \frac{(1+n_{(i)})(h_{m(i)} - h_{f(i)})}{(1+m_{(i)})(h_{m(i)} + n_{(i)}h_{m(i)} - n_{(i)}h_{l(i)})}\right] = P_{max(i)}\left(h_{m(i)} - \frac{n_{(i)}}{1+n_{(i)}}h_{l(i)}\right)\left[1 - \frac{(1+n_{(i)})(h_{m(i)} - h_{f(i)})}{(1+m_{(i)})(h_{m(i)} + n_{(i)}h_{m(i)} - n_{(i)}h_{l(i)})}\right]$$

wherein $U_{c(i)}$ represents the fracture energy of the i-th rock mineral during the nano-indentation experiment, in mN Wm; and step 1.3.6: based on the fracture energy for each rock mineral during the nano-indentation experiment, the elastic modulus of each rock mineral, and the contact area between the indenter in the rock nano-indentation experiment and the rock nano-indentation specimen, calculating plane-strain fracture toughness of each rock mineral according to the following formula:

$$K_{IC(i)} = \sqrt{\frac{U_{c(i)}E_{(i)}}{A_c}}$$

wherein $K_{IC(i)}$ represents the plane-strain fracture toughness of the i-th rock mineral, in $MPa \cdot m^{0.5}$.

5. The method for evaluating rock compressive strength based on cuttings mineral composition, nano-indentation, and friction tests according to claim 1, wherein the specific procedures of the step 1.5 are as follows:

step 1.5.1: collecting fresh cuttings from the studied formation, selecting blocky cuttings with the longest axis particle size of 0.8-1.2 cm, and grinding testing surfaces of the blocky cuttings to obtain a flat-surfaced cuttings specimen for friction testing;

step 1.5.2: fixing the cuttings specimen for friction testing onto a fixture of a friction and wear testing machine, performing the friction test on the cuttings under experimental conditions of a normal force of 10 N and a sliding speed of 0.1 mm/s, and recording friction force and normal force data; and step 1.5.3: calculating the friction coefficient based on the recorded friction force and normal force data from the cuttings friction testing according to the following formula:

$$\mu = \frac{F_f}{F_n}$$

wherein μ represents the rock friction coefficient, dimensionless; $F_f$ represents the friction force, in N; and $F_n$ represents the normal force, in N.

* * * * *